United States Patent
Holub et al.

(10) Patent No.: US 10,573,534 B2
(45) Date of Patent: Feb. 25, 2020

(54) RAPID HEATING PROCESS IN THE PRODUCTION OF SEMICONDUCTOR COMPONENTS

(71) Applicant: GLOBALFOUNDRIES Inc., Grand Cayman (KY)

(72) Inventors: Jan Holub, Weisswasser (DE); Kay Wendt, Weisswasser (DE)

(73) Assignee: GLOBALFOUNDRIES Inc., Grand Cayman (KY)

( * ) Notice: Subject to any disclaimer, the term of this patent is extended or adjusted under 35 U.S.C. 154(b) by 327 days.

(21) Appl. No.: 15/433,099

(22) Filed: Feb. 15, 2017

(65) Prior Publication Data

US 2017/0236721 A1    Aug. 17, 2017

(30) Foreign Application Priority Data

Feb. 15, 2016    (DE) .......... 10 2016 202 239

(51) Int. Cl.
| | | |
|---|---|---|
| H01L 21/324 | (2006.01) | |
| G01N 13/00 | (2006.01) | |
| G01B 11/24 | (2006.01) | |
| H01L 21/67 | (2006.01) | |
| H01L 21/66 | (2006.01) | |
| H01L 21/268 | (2006.01) | |
| H01L 21/84 | (2006.01) | |
| H01L 29/167 | (2006.01) | |
| H01L 29/34 | (2006.01) | |
| H01L 29/66 | (2006.01) | |

(52) U.S. Cl.
CPC .......... *H01L 21/3247* (2013.01); *G01B 11/24* (2013.01); *G01N 13/00* (2013.01); *H01L 21/268* (2013.01); *H01L 21/67248* (2013.01); *H01L 21/84* (2013.01); *H01L 22/10* (2013.01); *H01L 22/12* (2013.01); *H01L 22/20* (2013.01); *H01L 29/167* (2013.01); *H01L 29/34* (2013.01); *H01L 29/66568* (2013.01)

(58) Field of Classification Search
CPC ..... H01L 21/268; H01L 29/34; H01L 29/167; H01L 22/20; H01L 22/10; H01L 21/3247; H01L 29/66568; H01L 22/121; H01L 21/67248; H01L 21/84; G01N 13/00; G01B 11/24
See application file for complete search history.

(56) References Cited

U.S. PATENT DOCUMENTS

| | | | | |
|---|---|---|---|---|
| 7,038,773 B2 * | 5/2006 | Kuhlmann | ......... | G01N 21/9501 356/237.4 |
| 8,115,587 B2 * | 2/2012 | Koto | ....... | H01C 7/043 252/518.1 |

(Continued)

*Primary Examiner* — Savitri Mulpuri
(74) *Attorney, Agent, or Firm* — Amerson Law Firm, PLLC (57) ABSTRACT

A method for monitoring a rapid heating process to which a semiconductor wafer is subjected includes performing the heating process for a region of the semiconductor wafer, irradiating the semiconductor wafer with a laser beam, detecting light of the laser beam that is reflected from the semiconductor wafer, creating haze data based on the detected light and determining heated regions and/or transition regions between heated and non-heated regions of the semiconductor wafer on the basis of the haze data.

20 Claims, 4 Drawing Sheets

(56) References Cited

U.S. PATENT DOCUMENTS

| | | | | |
|---|---|---|---|---|
| 8,269,960 B2* | 9/2012 | Reich | .................. | G01N 21/9501 |
| | | | | 356/237.1 |
| 8,284,394 B2* | 10/2012 | Kirk | ................... | G01N 21/4738 |
| | | | | 356/237.1 |
| 8,422,010 B2* | 4/2013 | Kirk | ................... | G01N 21/4738 |
| | | | | 356/237.1 |
| 8,494,802 B2* | 7/2013 | Chen | .................. | G01N 21/9501 |
| | | | | 324/457 |
| 2008/0018887 A1* | 1/2008 | Chen | ...................... | G01N 21/47 |
| | | | | 356/237.2 |
| 2010/0190276 A1* | 7/2010 | Nakata | ............... | G01N 21/8422 |
| | | | | 438/16 |

* cited by examiner

RAPID HEATING PROCESS IN THE PRODUCTION OF SEMICONDUCTOR COMPONENTS

BACKGROUND

1. Field of the Disclosure

The present disclosure relates generally to the field of production of semiconductor components and integrated circuits, and, more particularly, to rapid heating processes, such as laser heating processes, and controlling them in the framework of the production of semiconductor components.

2. Description of the Related Art

In modern integrated circuits, a very large number of individual circuit elements, such as field effect transistors in the form of CMOS, NMOS, PMOS elements, resistors, capacitors and the like, are produced on a single chip surface. The structure dimensions of these circuit elements are typically continuously reduced following the introduction of every new circuit generation to provide currently available integrated circuits with improved performance in terms of speed and/or power consumption. Reducing the size of the transistors is an important aspect for the continued improvement of component performance in complex integrated circuits, such as CPUs. The reduction in size is typically associated with an increase in switching speed, thereby improving signal processing performance.

In addition to the large number of transistor elements, a plurality of passive circuit elements, such as capacitors and resistors, are typically also provided in an integrated circuit, as required by the basic circuitry structure. Due to the smaller dimensions of the circuit elements, not only the performance characteristics of the individual transistor elements are improved, but also their packing density is increased, as a result of which it is possible to incorporate more and more functions into a given chip surface. For this reason, very complex circuits have been developed, which may comprise different types of circuits, such as analog circuits, digital circuits and the like, thereby providing complete systems on a single chip (SoC).

Transistor elements can, in complex integrated circuits, be regarded as essential circuit elements, which determine the overall performance of the semiconductor components. In the course of continuous improvement of the performance of transistor elements, differently doped regions are formed in the semiconductor substrate, on and in which the transistor elements are formed. Activation of the dopants is generally affected by way of rapid heating processes (rapid thermal anneal), for example by way of lasers (laser anneal). For example, ultra-shallow junctions are provided in high-performance transistors of a certain class that contact the source/drain regions and extend partly below the gate electrode in the semiconductor substrate. Activation of the dopants in these junctions and of dopants in deep source/drain regions and halo regions can be affected by way of a very rapid and local laser heating process, so-called laser spike annealing (LSA), in which irradiation takes place over a period of a few milliseconds or less. However, the problem of accurately aligning such rapid local laser heating processes, such as LSA, arises, i.e., precisely positioning the laser exposure surface on the wafer to be processed. Only accurate alignment of the wafer with the laser beam and controlling the geometric shape and centering of a region on the wafer surface heated by laser annealing allows for reliable heating at, and only at, the desired position. In addition, the laser beam must be prevented from striking an edge of the wafer, since this can cause the wafer to fracture.

On the other hand, there is a growing need to utilize the wafer as completely as possible, i.e., to minimize the edge waste.

Inspection of the heated regions and, in particular, the transition regions of heated and non-heated regions on the wafer is conventionally performed by visual inspection of the wafer after it has been exposed to the heating process or with the aid of measuring its electrical resistance using, for example, 4-point probes. It is, therefore, made use of the fact that the electrical resistance strictly correlates with the heating temperature of the region on the wafer exposed to the heating. The visual inspection is disadvantageous because of the time required and the inherent inaccuracy or the subjective moment, respectively. The resistance measurement method is disadvantageous in that it is time-consuming and allows only for a limited resolution.

In view of the situation described above, the present disclosure relates to techniques of semiconductor manufacture using rapid heating processes, such as (rapid) laser heating and flash lamp heating, and to controlling such heating processes in the context of semiconductor manufacture.

SUMMARY OF THE DISCLOSURE

The following presents a simplified summary of the disclosure in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

In general, the present disclosure provides techniques in the context of the manufacture of semiconductor components, which comprise laser heating processes, in particular those with a duration of at most a few milliseconds, for example, a maximum of approximately one millisecond, hereinafter referred to as laser spike annealing (LSA). In particular, methods for monitoring/controlling such heating processes are provided. The heating process can heat the heated material to temperatures above 500° C. or 1000° C., for example, to temperatures in the range from approximately 500-1500° C., for example, in the range from 800-1400° C.

Among other things, the subject matter disclosed may include irradiating a wafer with a laser beam, detecting reflected light (scattered light and/or reflected light) from the wafer, and creating data based upon this detected light. This created data will be referred to in this specification as "haze data."

According to one illustrative embodiment of the present disclosure, a method for monitoring a rapid heating process to which a semiconductor wafer is subjected is provided. The method includes performing the heating process for a region of the semiconductor wafer and irradiating the semiconductor wafer with a laser beam. The method further includes detecting light of the laser beam that is reflected from the semiconductor wafer. Moreover, the method includes creating data representing light reflected/scattered from a surface of said semiconductor wafer on the basis of the light detected and determining at least one of heated regions and transition regions between heated and non-heated regions of the semiconductor wafer based on the created data. The created data may also be referred as "haze"

data as the term haze as used herein may be understood as being light that is reflected and/or scattered from the surface of wafer.

According to a further illustrative embodiment, a method for laser-heating a product semiconductor wafer is provided. The method includes irradiating the semiconductor wafer with a laser of a laser annealing system and adjusting the parameters of the laser annealing system such that a heated region on a production wafer is formed exactly and having a desired shape, where adjusting the parameters is effected on the basis of determining at least one of heated regions and transition regions between heated and non-heated regions of a semiconductor wafer.

In illustrative embodiments of the method specified above for monitoring a rapid heating process to which a semiconductor wafer is subjected, the method includes the steps of performing the heating process for a region of the semiconductor wafer, (subsequently) irradiating the semiconductor wafer with a laser beam, detecting light of the laser beam that is reflected from the semiconductor wafer, establishing haze data (maps) based on the detected light and determining heated (and possibly non-heated) regions, i.e., illuminated by the laser beam, and/or transition regions between heated and non-heated regions of the semiconductor wafer on the basis of the haze data.

As discussed above, the term "haze" refers to light that is reflected/scattered from the surface of the wafer. The position and shape of the region affected by laser annealing may be determined with an accuracy that is improved over prior art. The exact position of a transition region from a heated to a non-heated region may be determined by changing the signal strength of the haze data, i.e., the created data. According to the position determined, the control parameters of a laser annealing system may then be set such that a heated region on a production wafer is formed precisely and having the desired shape. Determining the heated regions may comprise determining properties thereof, such as the uniformity of a heated region.

It is in principle sufficient to provide a small number of anneal strips, approximately 1-5 anneal strips, for determining the heated and non-heated regions or transition regions, respectively, in order to determine the position and geometric shape of a surface heated on a wafer by a laser anneal process and in order to thus be able to optimize the alignment of the wafer with the laser annealing system. The above-mentioned method steps may therefore be performed for a test wafer and product wafers may—based on the results obtained with the test wafer—be subjected to an anneal process with precisely centered and circular heated regions which extend accurately up close to the edge of the circular product wafers.

It has been found that the heating process may change the surface properties of the semiconductor wafer, for example, a polysilicon wafer, in such a manner that the detection and analysis of light that is reflected from the surface of the semiconductor wafer may be used for determining the heated regions. For example, an optical inspection device may be used for this, which is conventionally used for detecting contamination particles on the surface of semiconductor wafers. The semiconductor wafer may be doped to facilitate the detection and analysis of the reflected light. Suitable dopants for this purpose are arsenic, polysilicon and boron, the latter being regarded as particularly suitable.

Determining the heated regions and, in particular, the transition regions between heated and non-heated regions may, according to the disclosure, be done based on haze data (maps), which may be obtained based on the reflected light.

The coordinates of haze data maps; i.e., the maps of the created data produced may be used to determine transition regions between heated and non-heated regions. The surface roughness, which correlates with the irradiation, may be encoded in a haze data map, as will be described later in more detail. Haze data, i.e., created data presenting light reflected and/or scattered from the surface of the semiconductor wafer, may here and hereafter be considered to be a measure of the surface roughness, but it may also be possible that the haze data reflects changes in the state of the material, for example, changes in the refractive index.

The laser beam may be scanned across the region of the semiconductor wafer to be heated and be emitted in a wavelength range of, for example, approximately 100-800 nm, and in particular, may represent a laser beam of light having essentially one wavelength in this range. The light beam may be a laser beam generated by a UV laser.

Compared to the method for determining heated regions and non-heated regions, or the transition region between them based on resistance measurements, as described above in the prior art, the method according to the present disclosure has the advantages of higher resolution, for example, below 50 μm or 25 μm, significantly higher speed and, avoiding any mechanical load due to the fact that no probe needs to contact the wafer surface. The higher resolution may be achieved by using the haze data (maps). Due to the higher resolutions, better repeatability on different systems may be achieved, as well as better control of overlay errors. Repeatability of inevitable overlay errors generated by LSA systems may be improved and the dispersion of such errors (especially among different LSA systems) may be reduced. In particular, a region of a production wafer being affected by laser annealing may therefore be mapped centered and formed having a round shape.

In one method, performing the heating process may include irradiating the region of the semiconductor wafer with a laser, where, in particular, the heating is effected in the form of laser spike annealing, in which heating may occur within a time period of a few milliseconds or a maximum of one millisecond.

A further illustrative embodiment may include determining the geometric shape and position of a surface of the semiconductor wafer heated by the heating process on the basis of the detected light that is reflected by the semiconductor wafer. The geometric shape and the position of a laser-generated exposure surface may therewith be determined should a laser be used for the heating process. Centering and adjusting the geometric shape may thereby be achieved.

In the above-described embodiments, detecting light that is reflected from the semiconductor wafer may comprise detecting light that is reflected prior to the heating process from the semiconductor wafer due to a first irradiation, and detecting light that is reflected after the heating process from the semiconductor wafer due to a second irradiation. Analysis of the reflected light may then comprise a comparison of the light detected prior to heating to the light detected after heating.

For example, the surface roughness of the semiconductor wafer may be determined on the basis of the detected light that is reflected from the semiconductor wafer, where the determination of the heated (and possibly non-heated) regions of the semiconductor wafer is based on the determined surface roughness. It may there be taken advantage of the fact that the surface roughness of the semiconductor wafer correlates with the temperature of the heating process and a magnitude for the surface roughness may therefore be obtained from the detected light. For example, the surface roughness may be encoded in a haze data map, and the heated (and possibly non-heated) regions of the semiconductor wafer may be determined based on the haze data map. A haze signal, i.e., a signal from light reflected/scattered from a surface, may there be obtained from the detected light that is reflected from the semiconductor wafer for every examined point of the semiconductor wafer, and mapping of the examined wafer region may be performed by use of the haze signals. "Haze" may there be defined as a decrease in the surface smoothness as compared to an ideally smooth surface. Visually, a wafer with a large average haze, i.e., with a large average amount of light reflected/scattered from the surface, is rather dull while a wafer with a small average haze, i.e., with a small average amount of light reflected/scattered from the surface, is rather shiny. The haze data map may be conditioned such that the data is cleaned from background noise, which is due to a natural roughness of an untreated semiconductor wafer. Haze that is caused by the natural roughness may be predetermined and filtered out from the data of the reflected light obtained. As already mentioned, however, the haze data determined from the reflected light may also represent changes in the state of the material, for example, changes in the refractive index.

Based on the reflected light detected, non-uniformities of an edge region of the semiconductor wafer irradiated by the laser beam and/or non-uniformities within an edge region of a scan strip of the laser beam and/or non-uniformities in the distances of adjacent scan strips of the laser beam may be determined by means of the haze data maps.

According to a further illustrative embodiment, the heating process for the region of the semiconductor wafer may be performed at a first temperature and subsequently a further heating process may be performed at least in a partial region of the region of the semiconductor wafer at a second temperature, where the second temperature is lower or higher than the first temperature. It has been found that the signal spacing in the haze data in the transition region from a heated region to a non-heated region may, due to the double heating process, be significantly improved, and determining the heated region may be improved on the basis of the haze data.

According to a further illustrative embodiment, the laser beam (in a strip, an anneal strip arises) may be scanned along a first line extending across the wafer in a first direction and crossing the region for which the heating process is carried out. It may thereby be possible to differentiate between heated and non-heated regions along the line. The laser beam may be scanned along a second line, which extends across the wafer in a second direction, which is perpendicular to the first direction and which crosses the region for which the heating process is carried out.

According to a further illustrative embodiment, the detection of the light that is reflected from the semiconductor wafer may comprise the generation of detection signals with signal amplitudes, and the heated (and possibly non-heated) regions of the semiconductor wafer may be detected only on the basis of such detection signals where the amplitude of which is below a predetermined amplitude limit, wherein, in particular, detection signals with amplitudes above the predetermined amplitude limit indicate contaminations of the semiconductor wafer with dirt particles. In other words, a rather low-frequency range of the detected spectrum may be used for determining the heated and non-heated regions of the semiconductor wafer, respectively, whereas a rather high-frequency region of the spectrum may be evidence for the presence of dirt particles on the surface of the semiconductor wafer.

On the basis of the findings obtained from the above-described methods, heating processes may be performed with other production wafers to be processed.

According to a further illustrative embodiment of the present disclosure a method for manufacturing a semiconductor component is provided. The method includes providing a semiconductor wafer and forming a layer of the semiconductor component in at least one of the wafer and on a surface of the semiconductor wafer. The method further includes heating a region of the layer in a rapid heating process and irradiating the semiconductor wafer with a laser beam. Moreover, the method includes detecting light of the laser beam that is reflected from the semiconductor wafer and creating data on the basis of the light detected, wherein the data represent light reflected/scattered from the surface of the semiconductor wafer. Furthermore, the method includes determining heated and non-heated regions of the semiconductor wafer based on the established created data and adjusting the heating process, if the particular heated and non-heated regions do not meet predetermined criteria, such that at least one of the geometric shape and centering of a surface irradiated by the laser on the semiconductor wafer is controlled in a desired manner.

This manufacturing method may include the steps of the above-described methods for monitoring/controlling a heating process. The semiconductor wafer may comprise a SOI (silicon-on-insulator or semiconductor-on-insulator) or FDSOI (fully depleted SOI) semiconductor substrate that is composed of a semiconductor substrate, a buried insulating layer formed thereon, such as a buried oxide layer, and a semiconductor layer formed thereon. The semiconductor component may comprise a transistor component, for example, a FET, MOSFET, and forming the layer may include forming a doped layer of a transistor component and heating the region of the layer may include activating dopants of the doped layer. The doped layer may be formed in a semiconductor layer of the semiconductor wafer. The heating may again be done in the form of a laser spike annealing.

Adjusting the heating process may include changing at least one of the shape and the position of a surface on the semiconductor wafer irradiated by a laser for heating. This may be effected by way of a respective modification/adaptation of an optical system used for guiding the laser beam.

Furthermore, a further illustrative embodiment may include determining the contamination of the semiconductor wafer with contamination particles based on the detected light that is reflected from the semiconductor wafer. Firstly, findings about the contamination of the semiconductor wafer and, secondly, about the heated regions may be gained from the same spectrum of the reflected light obtained. The signal values above a predetermined limit may be used for particle detection and below the predetermined limit the values may be used for determining the heated regions.

BRIEF DESCRIPTION OF THE DRAWINGS

The disclosure may be understood by reference to the following description taken in conjunction with the accompanying drawings, in which like reference numerals identify like elements, and in which.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present disclosure will now be described with reference to the attached figures. Various structures, systems and devices are schematically depicted in the drawings for purposes of explanation only and so as to not obscure the present disclosure with details which are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary or customary meaning as understood by those skilled in the art, is intended to be implied by consistent usage of the term or phrase herein. To the extent that a term or phrase is intended to have a special meaning, i.e., a meaning other than that understood by skilled artisans, such a special definition shall be expressively set forth in the specification in a definitional manner that directly and unequivocally provides the special definition for the term or phrase.

As is readily appreciated by the person skilled in the art upon completely reading the present application, the present methods are applicable to several technologies, such as NMOS, PMOS, CMOS, etc., and are applicable to various components including, but not limited to, logic components, memory devices, etc.

The present disclosure provides methods for monitoring/controlling heating processes in the manufacture of semiconductors and methods for manufacturing semiconductor components by use of heating processes. The surface of a semiconductor wafer treated in a heating process is analyzed by way of detected light that is reflected from the semiconductor wafer after irradiation of the latter. Illustrative embodiments of the present disclosure shall now be described in more detail with reference to the accompanying drawings.

Figure 1:
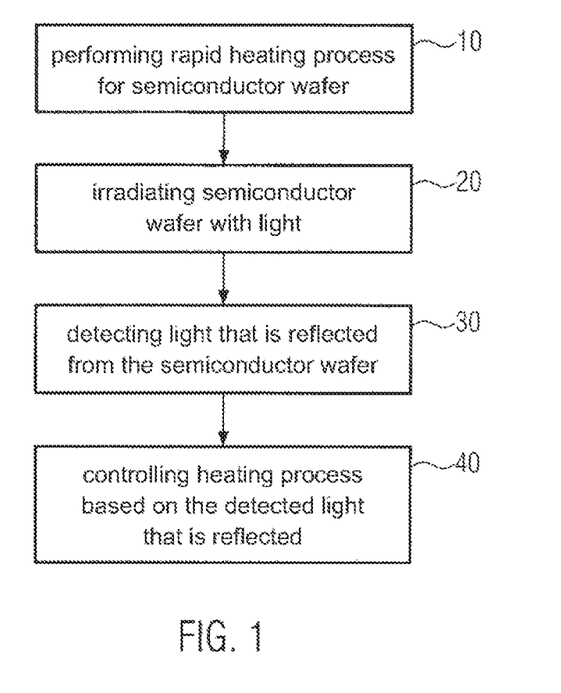
FIG. 1 is a flow diagram illustrating an embodiment of a method of the present disclosure.

FIG. 1 shows an embodiment of a method according to the disclosure in the form of a flow diagram. A semiconductor wafer is locally subjected to a rapid heating process 10. The rapid heating process may be laser spike annealing. The wafer may comprise a semiconductor substrate over which a semiconductor layer is formed. A buried insulating layer may be provided between the semiconductor layer and the substrate, thereby providing an SOI configuration. The substrate and the semiconductor layer may each be made of material containing silicon in which other components, such as germanium, carbon and the like, may be incorporated to provide desired electronic properties.

After termination of the heating process, the surface of the semiconductor wafer is irradiated 20 with light. Irradiation is effected, for example, by laser scanning, for example, with monochromatic light having a wavelength in the range from 100-800 nm. Irradiation 20 may be effected by use of an optical measuring device comprising a light source, for example, in the form of a laser, and a detection device for detecting reflected light. The light emitted from the surface of the irradiated semiconductor wafer is detected 30 and analyzed. The heating process may thus be controlled 40 on the basis of the emitted light that is detected. It is, therefore, essential that the light emitted contains information about the surface of the semiconductor wafer. The detected light may be converted to contain information on the roughness of the surface of the semiconductor wafer. Since, for example, the roughness correlates with the temperature of the heating process, heated and non-heated regions of the semiconductor wafer may thus be determined on the basis of the signals. The regions which have been heated during the heating process may have a larger haze i.e., a larger amount of light reflected/scattered from the surface of the semiconductor wafer (for example a higher roughness) than those regions which have not been heated. As previously discussed, the term "haze" is representing light reflected and/or scattered from a surface of said semiconductor wafer.

Undesired non-uniform heating of a target region, any defocusing or geometric deformation of a heated region of a wafer, etc. may thus be detected by use of the data of the detected light that is reflected (for example, from data of a haze map, i.e. a map representing light reflected/scattered from the surface of the semiconductor wafer, created for an examined region of the semiconductor wafer) (for haze mapping see, for example, WO 2004/105087). The haze data may also reflect properties other than the surface roughness, for example, changes in state of the material, for example, changes in the refractive index.

Due to the specific heated and non-heated regions or the transition regions between these regions, respectively, the annealing process for the production wafers may be adjusted by way of a corresponding adjustment of the parameters of a laser annealing system in such a way that a heated region on the production wafer may be formed precisely and having the desired shape. A well-controlled annealing process may thus be performed in the production process. The annealing process may serve to activate dopants in the framework of manufacturing a semiconductor component on and in the semiconductor wafer. For example, it may serve to form halo regions, deep source/drain regions and/or ultra-shallow junctions in the production of (MOS) FETs.

Figure 2:
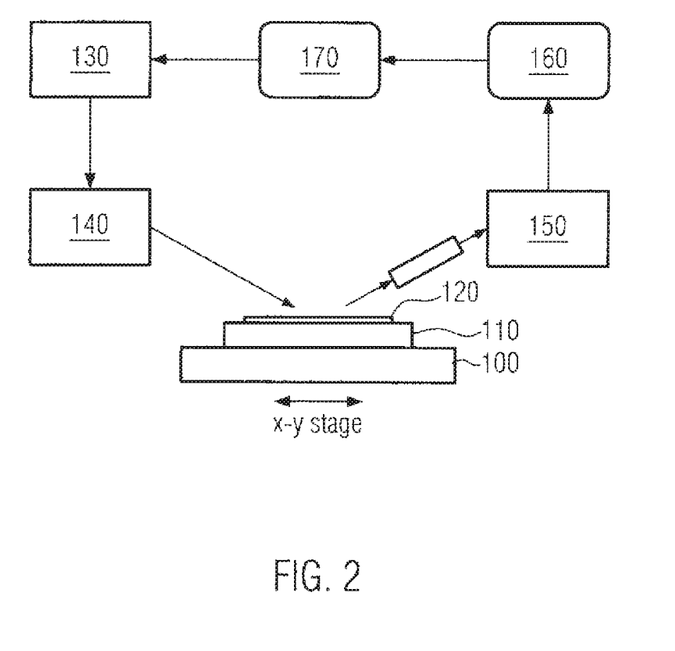
FIG. 2 shows an exemplary device for rapid local laser heating of a region of a semiconductor wafer.

FIG. 2 shows an exemplary device for rapid local laser heating of a region of a semiconductor wafer that may be employed in the method according to the disclosure. The device shown in FIG. 2 may be used for performing step 10 shown in FIG. 1. The device comprises a movable stage 100 with a wafer holder 110, for example a hot chuck, for holding a semiconductor wafer 120 to be locally subjected to the heating process.

Heating may be effected by way of a laser 130, for example, a $CO_2$ laser. The light emitted from laser 130 is via an optical system 140 directed onto the semiconductor wafer 120. Light emitted from the semiconductor wafer 120 may be detected with a detector 150. The detector 150 may be connected to a processing device 160 which, on the basis of the data delivered by the detector 150, may determine a temperature of the region of the semiconductor wafer 120 irradiated by the laser 130 and supply data about the specific temperature to a control device 170. The control device 170 may control the laser 130 in a feedback manner based on the data regarding the specific temperature obtained from the processing device 160.

Figure 3:
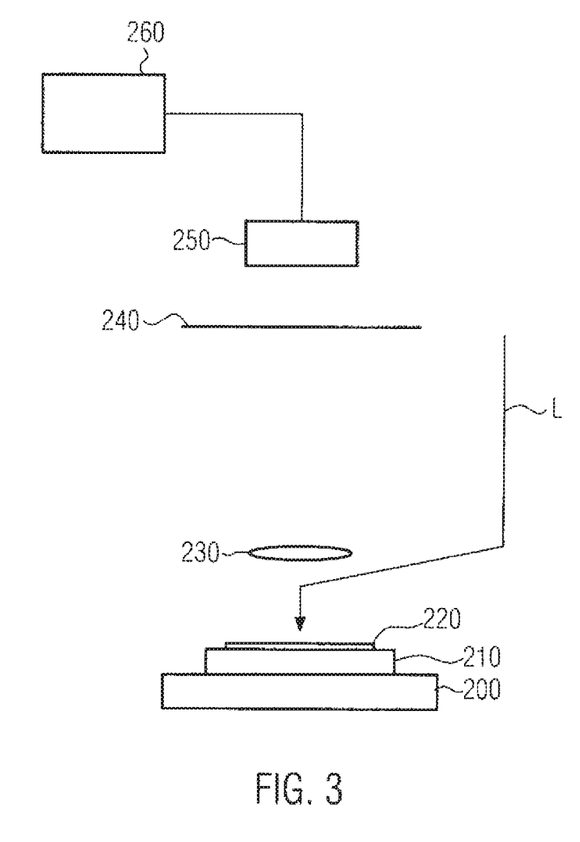
FIG. 3 shows an exemplary device for detecting and analyzing light that is reflected from an irradiated semiconductor wafer.

FIG. 3 shows a measuring device which may be used in embodiments according to the disclosure. The measuring device shown in FIG. 3 may be used for performing steps 20, 30 and 40 shown in FIG. 1. The measuring device may comprise a stage 200 with a wafer holder 210 for holding a semiconductor wafer 220 to be examined. A laser beam L may, with the aid of an optical system (not shown), be directed onto the semiconductor wafer 220. The laser beam L may be guided so as to strike the surface of the semiconductor wafer 220 perpendicularly)(90°), or it may be guided to strike the surface of the semiconductor wafer 220 at a finite oblique angle between 0° and 90°.

The measuring device may further comprise a lens collector 230 for collecting light that is reflected from the surface of the semiconductor wafer 220. In addition, an elliptical collector may be provided above the semiconductor wafer 220 and surrounding the lens collector 230. The reflected light collected by the lens collector 230 passes through apertures 240 and an optional polarizer to a detector 250. The detector 250 may be a dark field collector. The detector 250 may be connected to a data processing device 260 which may process the data provided by the detector 250 for analysis and enable performing step 40 shown in FIG. 1. Based on the data provided by the detector 250, haze data maps may be created with the aid of the data processing device 260 and heated regions of the semiconductor wafer 220 may be determined. For a haze data map, a line scan may be performed along a previously defined line (i.e., the data of the haze data map may be read out along the predetermined line), and the data of the line scan (haze level along the line) may be used to determine heated and non-heated regions or transition regions between heated and non-heated regions, respectively. The distance of a heated region from the edge may be accurately determined. Depending on the recipe, for example, one or more anneal strips may be created by the laser on the wafer and the line scan may be performed both along as well as perpendicular to the strip or strips. Depending on the recipe, arc-shaped anneal strips may be created by the laser at edge regions of the wafer and the line scan may as well be performed both along as well as perpendicular to the strips. A low-pass filter may be used to increase the signal-to-noise ratio.

A conventional particle measuring device, such as the KLA Surfscan® SP3 or KLA SURFmonitor, may be used to create the haze map data.

Figure 4:
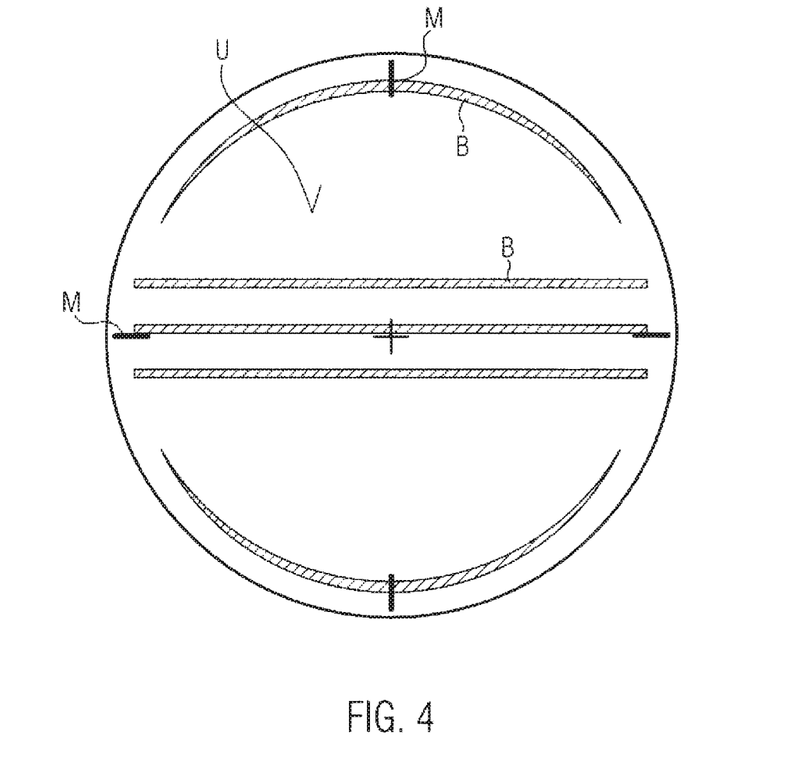
FIG. 4 shows a wafer irradiated according to an exemplary recipe which has heated regions and non-heated regions that can be precisely determined using haze data maps.

FIG. 4 by way of illustration shows a wafer irradiated according to one exemplary recipe and comprising heated regions B that comprise arc-shaped heated regions and horizontal strips, and non-heated regions U (or the transitions between them) which may by way of haze data maps be accurately determined. The above-mentioned line scans may be performed along vertical and horizontal lines extending between markings M. Adjustment of a laser annealing system may be effected on the basis of the findings with respect to the exact position of irradiated regions B obtained via the irradiated wafer shown. In the recipe illustrated, but also in any other recipe which is regarded as being suitable, a double annealing process may be performed in each or in some anneal strips. A first annealing process may be performed at a first temperature, for example at approximately 1100° C., and a second annealing process may be performed within the strip thus formed at a second temperature, for example, at approximately 1230° C. Alternatively, the first annealing process may be performed at a higher temperature than the second one. The double annealing process may achieve larger signal spacing of the haze measurement data in transition regions between heated regions B and non-heated regions U (i.e., the haze data values of heated regions B are more distinct from the haze data values of non-heated regions U), whereby determining the exact position of these transition regions may further be improved.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Note that the use of terms, such as "first," "second," "third" or "fourth" to describe various processes or structures in this specification and in the attached claims is only used as a short-hand reference to such steps/structures and does not necessarily imply that such steps/structures are performed/formed in that ordered sequence. Of course, depending upon the exact claim language, an ordered sequence of such processes may or may not be required. Accordingly, the protection sought herein is as set forth in the claims below.

What is claimed:

1. A method for monitoring a rapid heating process to which a semiconductor wafer is subjected, comprising:
   performing said heating process for a region of said semiconductor wafer, wherein said heating process for said region is performed at a first temperature;
   irradiating said semiconductor wafer with a laser beam;
   detecting light of said laser beam that is at least one of reflected and scattered from a surface of said semiconductor wafer;
   creating data on the basis of said light detected;
   determining at least one of heated regions and transition regions between heated and non-heated regions of said semiconductor wafer based on said created data; and
   performing a further heating process at least in a partial region of said region of said semiconductor wafer at a second temperature that is different from said first temperature after performing said heating process.

2. The method of claim 1, further comprising determining the geometric shape and position of a surface of said semiconductor wafer heated in said heating process on the basis of said detected light that is at least one of reflected and scattered by said surface of said semiconductor wafer.

3. The method of claim 1, wherein performing said heating process comprises irradiating said region with a laser, and wherein said heating is performed in the form of laser spike annealing.

4. The method of claim 1, wherein detecting said light comprises detecting light that is reflected prior to said heating process from said semiconductor wafer due to a first irradiation, and detecting light that is reflected after said heating process from said semiconductor wafer due to a second irradiation.

5. The method of claim 1, further comprising determining a surface roughness of said semiconductor wafer on the basis of the detected light, and wherein determining said heated regions of said semiconductor wafer is based on the determined surface roughness.

6. The method of claim 5, wherein the surface roughness is encoded in a map of said created data, and said heated regions of said semiconductor wafer are determined based on said map of said created data.

7. The method of claim 1, further comprising doping the wafer with at least one of arsenic and boron.

8. The method of claim 1, wherein said laser beam is scanned along a first line extending across said wafer in a first direction and crossing the region for which said heating process is performed.

9. The method of claim 8, wherein said laser beam is scanned along a second line extending across said wafer in a second direction that is perpendicular to said first direction and crossing the region for which said heating process is performed.

10. The method of claim 1, wherein the detection of said light comprises generating detection signals with signal amplitudes, and wherein determining the heated regions of said semiconductor wafer is effected only on the basis of such detection signals, the amplitude of which is below a predetermined amplitude limit, where detection signals with amplitudes above said predetermined amplitude limit indicate contaminations of said semiconductor wafer with dirt particles.

11. The method of claim 1, further comprising at least one of filtering said created data by use of a low-pass filter and low-pass filtering detected measurement values.

12. The method of claim 1, further comprising controlling an overlay error.

13. The method of claim 1, wherein said created data comprises at least one of a surface roughness and a refractive index.

14. A method for manufacturing a semiconductor component, comprising:
providing a semiconductor wafer;
forming a layer of said semiconductor component in at least one of said wafer and on a surface of said semiconductor wafer;
heating a region of said layer in a heating process;
irradiating said semiconductor wafer with a laser beam;
detecting light of said laser beam that is at least one of reflected and scattered from a surface of said semiconductor wafer;
creating data on the basis of said light detected;
determining heated and non-heated regions of said semiconductor wafer based on said created data; and
if the determined heated and non-heated regions do not meet predetermined criteria, adjusting the heating process such that at least one of the geometric shape and a centering of a surface irradiated by said laser on said semiconductor wafer is controlled in a desired manner.

15. The method of claim 14, wherein forming said layer comprises forming a doped layer of a transistor component and heating the region of said layer comprises activating dopants of said doped layer.

16. The method of claim 14, wherein the heating process comprises performing a laser spike anneal with the aid of a laser.

17. The method of claim 14, further comprising determining a contamination of said semiconductor wafer with particles based on the detected light.

18. The method of claim 14, wherein said semiconductor wafer comprises one of an SOI and an FDSOI semiconductor substrate.

19. A method for monitoring a rapid heating process to which a semiconductor wafer is subjected, comprising:
performing said heating process for a region of said semiconductor wafer;
irradiating said semiconductor wafer with a laser beam;
detecting light of said laser beam that is at least one of reflected and scattered from a surface of said semiconductor wafer, wherein detecting said light comprises detecting light that is reflected prior to said heating process from said semiconductor wafer due to a first irradiation, and detecting light that is reflected after said heating process from said semiconductor wafer due to a second irradiation;
creating data on the basis of said light detected; and
determining at least one of heated regions and transition regions between heated and non-heated regions of said semiconductor wafer based on said created data.

20. The method of claim 1, further comprising determining at least one of non-uniformities of an edge region of said semiconductor wafer irradiated by said light beam and non-uniformities within an edge region of a scan strip of said light beam on the basis of said detected light.

* * * * *